United States Patent
Benicewicz et al.

(10) Patent No.: US 6,762,836 B2
(45) Date of Patent: Jul. 13, 2004

(54) PORTABLE LASER PLASMA SPECTROSCOPY APPARATUS AND METHOD FOR IN SITU IDENTIFICATION OF DEPOSITS

(75) Inventors: Pamela Benicewicz, Loudonville, NY (US); Andrew Joseph Travaly, Ballston Spa, NY (US); Pingfan Wu, Willingboro, NJ (US); Elena Rozier, Schenectady, NY (US)

(73) Assignee: General Electric Company, Schenectady, NY (US)

( * ) Notice: Subject to any disclaimer, the term of this patent is extended or adjusted under 35 U.S.C. 154(b) by 111 days.

(21) Appl. No.: 10/152,349

(22) Filed: May 22, 2002

(65) Prior Publication Data

US 2003/0218745 A1 Nov. 27, 2003

(51) Int. Cl.[7] ............................. G01J 3/30; G01N 21/00
(52) U.S. Cl. ..................................... 356/318; 356/237.3
(58) Field of Search ............................... 356/318, 237.3

(56) References Cited

U.S. PATENT DOCUMENTS

| | | | |
|---|---|---|---|
| 5,531,857 A | * | 7/1996 | Engelsberg et al. ...... 156/345.5 |
| 5,608,520 A | * | 3/1997 | Fleming ..................... 356/318 |
| 5,715,053 A | | 2/1998 | Loge |
| 5,751,416 A | | 5/1998 | Singh et al. |
| 5,757,484 A | | 5/1998 | Miles et al. |
| 5,798,832 A | | 8/1998 | Hnilica et al. |
| 5,814,156 A | * | 9/1998 | Elliott et al. .................... 134/1 |
| 5,847,825 A | * | 12/1998 | Alexander .................. 356/318 |
| 5,946,089 A | * | 8/1999 | Duer .......................... 356/318 |
| 6,008,896 A | | 12/1999 | Sabsabi et al. |
| 6,147,754 A | | 11/2000 | Theriault et al. |
| 6,366,353 B1 | * | 4/2002 | Brown et al. ................ 356/318 |
| 2003/0085203 A1 | * | 5/2003 | Nair et al. ................ 219/121.6 |
| 2003/0147072 A1 | * | 8/2003 | Whitehouse ................ 356/318 |

FOREIGN PATENT DOCUMENTS

WO     WO 99/46368     9/1999

\* cited by examiner

*Primary Examiner*—F. L. Evans
*Assistant Examiner*—Kara Geisel
(74) *Attorney, Agent, or Firm*—Nixon & Vanderhye PC

(57) ABSTRACT

A portable Laser Plasma Spectroscopy (LPS) system and process is provided for performing in situ, near-real time, remote elemental analysis and identification of deposits or other foreign material found on surfaces of machine parts, such as turbine compressor blades or the like, wherein identification of the elemental constituents of a particular deposit is obtained without incurring significant ablative damage to the machine part substrate material underlying the deposit.

21 Claims, 3 Drawing Sheets

PORTABLE LASER PLASMA SPECTROSCOPY APPARATUS AND METHOD FOR IN SITU IDENTIFICATION OF DEPOSITS

The present invention generally relates to the elemental analysis of deposits found on surfaces of machinery parts and components. More particularly, the present invention relates to an in situ laser plasma spectroscopy (LPS) analysis and identification of material deposits found on the surfaces of power generating equipment components such as gas turbine compressor blades.

BACKGROUND OF THE INVENTION

Unknown contaminants and/or deposits may be found accumulating on the surfaces of various parts and components of power generating machines and equipment, e.g., on compressor blades of turbine engines, during the ordinary course of operation. Such deposits have a potential for inducing performance degradation and component damage. For example, in the case of a gas turbine compressor, such deposits may significantly affect the airflow and overall operating efficiency. If the composition and character of such a deposit is known, an appropriate corrective action may be taken. However, such deposits often occur on parts and components that are relatively inaccessible without substantial disassembly of the particular apparatus or equipment involved.

Using conventional analysis techniques and tools, at least a partial disassembly of an apparatus and/or removal of an affected part is often required in order to gain access to the deposit or surface contaminant for performing an analysis. In the case of large power generating equipment, such as a gas turbine compressor, the time and cost of performing even a partial disassembly can be enormous. Consequently, there is a need for a more practical and economical means for performing analysis of deposits found on component surfaces of machinery without requiring substantial disassembly of such.

Laser Plasma Spectroscopy (LPS), also known as Laser-Induced Breakdown Spectroscopy (LIBS) or Laser-Induced Plasma Spectroscopy (LIPS) (as well as by other names) is a well-understood technique for performing both qualitative and quantitative elemental analysis of materials and compounds. Such LPS techniques may be used more or less effectively for procuring elemental analysis of many different substances including compounds in the form of gases, liquids or solids. In accordance with the basic technique, the light output from a pulsed laser is focused onto the surface of an object. Assuming the focused laser pulse has sufficient intensity, a small amount of material at the surface of the object is vaporized forming a high-temperature plasma consisting of ions and excited atoms that emit a particular spectrum of light radiation which corresponds to elemental constituents of the vaporized material. The elemental composition of the irradiated material may then be accurately determined through spectral analysis of light radiation emitted from the plasma. Multiple plasma generating laser pulses are often used in succession to obtain additional spectral data to improve the accuracy of the analysis.

LPS also has certain advantages over other types of elemental analytical techniques. For example, when using an LPS technique for elemental analysis, extensive preparation of a sample to be analyzed is not required and only a small quantity of the sample material (e.g., on the order of nanograms) is vaporized during analysis. In addition, an LPS analysis may be performed fairly rapidly. A plasma adequate for producing a spectrum sufficiently luminous to enable elemental identification via spectroscopy may be obtained using only a single laser pulse. Moreover, since many different wavelengths from the plasma spectrum may be simultaneously analyzed, multiple constituent elements may be identified at the same time.

Laser plasma spectroscopy (LPS) has proven to be useful in a variety of different laboratory and industrial applications. See, for example, the following U.S. patents: U.S. Pat. No. 6,008,896 to Sabsabi et al. entitled "Method And Apparatus For Spectroscopic Analysis of Heterogeneous Materials", issued Dec. 28, 1999; U.S. Pat. No. 5,798,832 to Hnilica et al. entitled "Process And Device For Determining Element Compositions And Concentrations", issued Aug. 25, 1998; U.S. Pat. No. 5,751,416 to Singh et al. entitled "Analytical Method Using Laser-Induced Breakdown Spectroscopy", issued May 12, 1998; International Patent No. WO 99/45368 to Nelson et al. entitled "Improved Laser Spectral Analyzer With Sample Location Detector", published Sep. 10, 1999; U.S. Pat. No. 5,757,484 to Miles et al. entitled "Standoff Laser Induced-Breakdown Spectroscopy Penetrometer System", issued May 26; U.S. Pat. No. 6,147,754 to Theriault et al. entitled "Laser Induced Breakdown Spectroscopy Soil Contamination Probe", issued Nov. 14, 2000; and U.S. Pat. No. 5,715,053 to Loge entitled "Method For Determining The Concentration of Atomic species In Gases And Solids", issued Feb. 3, 1998. However, the conventional LPS techniques disclosed in the above mentioned patents have various drawbacks which tend to render them unsuitable for use in the identification of surface deposits found on machinery and, in particular, on components of power generating equipment and the like.

Although LPS is generally recognized as a valid technique for analyzing and identifying the elemental compositional makeup of various materials, there exists a problem in that an object being examined using LPS may suffer significant damage by continued firing of the laser. For example, surface damage incurred through ablation by the laser during an LPS process may significantly reduce the lifetime of a gas turbine compressor blade. In addition, conventional LPS systems are not readily portable and are not generally convenient to use at the location sites of power generating equipment. Many LPS systems are large and rather bulky. Also, the plasma generating laser light output of many LPS systems is not easy to direct and focus onto a particular target, especially if that target is within a relatively small or confined area or is at a location or part within a larger machine and is difficult to see and/or reach. Moreover, conventional LPS systems typically do not provide rapid analysis of LPS data and make that analysis available to a user in near real-time while at the location of the equipment or machinery being examined.

BRIEF DESCRIPTION OF THE INVENTION

In one aspect of the present invention, a portable system and method is provided that allows in situ testing and near-real time elemental analysis and identification of deposits or other contaminants found on the surfaces of machine parts or other objects wherein minimal or no damage to the substrate material beneath the deposit is incurred as a result of the testing and analysis procedures. Elemental identification is based on a technique of laser plasma spectroscopy (LPS), to wit: a technique wherein the output of a high peak power pulsed laser is focused to a small spot on an object surface sufficient to result in the vaporization of material within the focal volume of the laser pulse and the formation of a luminous plasma which is spectrally analyzed to identify the elemental composition.

In an example embodiment of the invention, a time-resolved spectral profile of the light radiation emitted from one or more plasma events created from a surface deposit during LPS is obtained using a gated PDA (photo-diode array) or ICCD (intensified charge-coupled device) detector coupled to a portable spectrometer. The laser light used for producing the plasma is electronically shuttered (blocked) upon detection of the elemental profile of the particular substrate material belonging to the machine part or object on which a found deposit is being analyzed. The shuttering is initiated after no more than one laser pulse has hit the substrate, prior to the occurrence of any significant ablation damage to the part. Acquisition, storage and analysis of plasma spectral data acquired from the detector is accomplished in situ using a portable or hand-held computer or like device, which is also used to display a spectral intensity profile of the plasma. In addition, the portable computer device is, or may be, programmed to identify the elemental composition of the deposit through comparison analysis with known spectral profiles that are either stored within the computer or accessed, for example, via a telecom link from a remote database.

In accordance with another aspect of the present invention, analysis of the plasma spectrum may be performed at a location that is effectively "remote" from the site of generated plasma on a machine part or other object. A fiber-optic probe or borescope is used to transmit the light from the laser source to a location of interest, such as on a machine part, and to return plasma light radiation emissions back to a spectrometer and detector. In this regard, a further beneficial aspect of the present invention is that it facilitates diagnostic access to parts of a turbine compressor (or other machinery) that are ordinarily difficult to access, thus precluding the need for any substantial disassembly of the object or machinery under examination.

In another aspect of the present invention, the LPS system is able to resolve, both spectrally and temporally, emissions from a plasma generated primarily from only the substantive material of an examined deposit present on the surface of an examined machine component or object and without producing any significant ablation damage to the machine component or object itself.

Yet another beneficial aspect of the present invention is that it substantially reduces the possibility that the surface of an examined object or machine component might sustain damage caused by ablation from the laser during an LPS process.

DETAILED DESCRIPTION OF THE INVENTION

Figure 1:
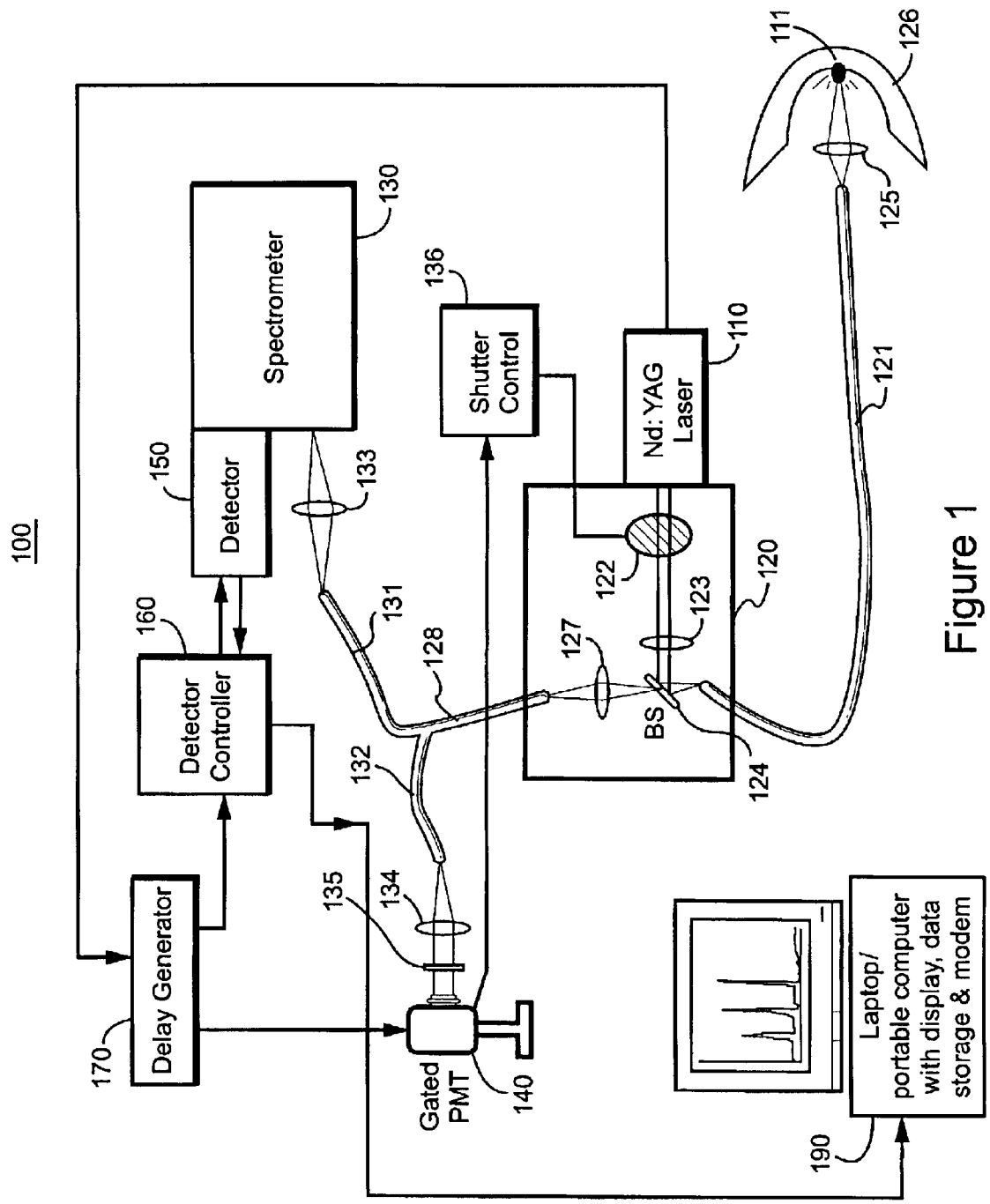
FIG. 1 is a system block diagram of an example embodiment of the invention, and which may be used to practice an embodiment of the method of the invention.

FIG. 1 shows a block diagram of an example portable diagnostic system 100 for performing laser plasma spectroscopy (LPS) on a surface deposit found on an object or machine part such as, for example, a gas turbine compressor blade. As is typical in LPS systems, one or multiple pulses of light from a Nd:YAG laser (110) at its fundamental wavelength or any of its harmonic wavelengths, or any high peak power pulsed laser capable of generating sufficiently high focused intensities—are used to vaporize material from an object to generate a luminous plasma 111 for spectral analysis. In this example system, Nd:YAG laser 110 is of a type that is compact, portable and capable of generating light pulse intensities on the order of 1 $GW/cm^2$ or greater. A light impenetrable safety housing 120 may also be provided for enclosing at least the optical components of system 100 to preclude any inadvertent exposure of a user to Class IV laser light.

The output from laser 110 passes through focusing lens 123 and is then reflected by beam splitter 124 into optical fiber 121. Lens 123 focuses the output of laser 110 into optical fiber 121 in a manner that optimizes the coupling of the laser beam to the fiber. Beam splitter 124 is designed and manufactured such that it reflects light at the output wavelength of laser 110 (e.g., 1064 nm) but transmits light within a predetermined bandwidth of the emission spectrum of light radiation from plasma 111 (typically in the range of 300-900 nm).

Although not explicitly illustrated in FIG. 1, optical fiber 121 is encased in a flexible casing or sheath that also functions as a protective housing for focusing lens 125 which is located at the opposite end of fiber 121. Lens 125 is used to focus the laser light exiting optical fiber 121 onto the surface of the object being analyzed—such as, for example, the surface of a compressor blade (126). Preferably, the casing or sheath used to house both optical fiber 121 and lens 125 extends beyond lens 125 for a distance equal to the focal distance of lens 125 so that a proper and consistent focus of laser light energy onto the object surface is maintained whenever the laser light output end of the fiber casing is placed in contact with the object surface.

When a focused laser pulse of sufficient intensity (1 $GW/cm^2$ or greater per output pulse is typically sufficient for most applications) strikes the part surface, a small quantity of surface material of object 126 that lies within the focal volume of lens 125 is vaporized, forming a high-temperature luminous plasma (111). Light radiation emanating from the plasma plume is then collected, also by lens 125 and coupled to optical fiber 121. After traveling through optical fiber 121, light from the plasma exits the fiber and passes through beam splitter 124. Lens 127 collects the plasma light and couples it to a second bifurcated optical fiber 128.

This second optical fiber is bifurcated at a point along its length into two branch portions 131 and 132 and is constructed such that a majority of the plasma light radiation collected by the fiber optic probe 121 for spectral analysis is directed by branch 131 to spectrometer 130 and a small predetermined portion of the plasma light radiation is directed via branch 132 to photo-multiplier tube (PMT) 140. For example, 90% of the collected plasma light radiation entering the fiber may be directed to spectrometer 130 via fiber portion 131 and 10% of the collected plasma light radiation may be directed to photo-multiplier tube (PMT) 140 via fiber portion 132. As one of ordinary skill in the art may recognize, rather than using a bifurcated fiber, other means for diverting a portion of the collected plasma light to the spectrometer and a portion to the PMT may be used. For example, in an alternative embodiment, a beam splitter or the like may be used to pass most of the collected plasma light radiation to the spectrometer 130 and to reflect a predetermined smaller portion of the plasma light radiation to photo-multiplier tube 140. Likewise, one of ordinary skill in the art will appreciate that other types of low light level detecting devices of properties similar to a photo-multiplier tube may also be used in place of PMT 140.

Plasma light radiation provided to spectrometer 130 from bifurcated fiber portion 131 is focused by lens 133 onto a front entrance slit (not shown) of spectrometer 130. Upon passing through spectrometer 130, the light is spectrally dispersed and focused onto the front face of a semiconductor array detector 150, which may comprise, for example, a conventional photo-diode array (PDA) or an intensified charge-coupled device (ICCD). Other types of detectors of similar properties may also be used.

A smaller percentage of the collected plasma light radiation is directed by fiber optic portion 132 to PMT 140 via lens 134 and passes through optical filter 135. This portion of the light is collected and collimated by lens 134 through an optical bandpass filter arrangement 135 onto a light sensitive portion of PMT 140. Bandpass filter 135 is constructed such that only predetermined narrow bandwidths of light reach PMT 140. With this arrangement, the elemental atomic emission spectra from other materials, for example, deposits vaporized from the surface of the object, will not be passed to PMT 140.

The predetermined narrow bandpass of filter 135 is selected so as to transmit only a narrow range of selected wavelengths that encompasses an atomic emission or emissions from the object whose surface deposits are being sampled. Bandpass filter 135 may consist of, for example, a conventional Fabry-Perot interference filter having a very narrow transmission bandwidth (e.g., 1-10 nm). Alternatively, one may use a tunable acousto-optic filter to transmit wavelengths within a narrow band (~4 nm), where the central wavelength of such narrow band can be varied depending on the particular atomic emission that is to be transmitted. Although not depicted in FIG. 1 as such, these optical components, including lenses 133, 134 and bifurcated fiber 128 (or its equivalent), may also be configured as a part of optical system enclosure 120.

The laser power supply generates an electronic TTL output pulse which is synchronized to the emission of a laser pulse and is used to trigger an adjustable delay generator (170) which, after predetermined delays, sends a triggering signal to detector controller 160 and a pulse of adjustable width to gated PMT 140. Detector controller 160 may comprise conventional logic circuitry for controlling the collection and output of data from a PDA or an ICCD detector of the type conventionally used with a spectrometer. The detector controller activates spectrometer detector 150 for a predetermined duration at a predetermined time after formation of the plasma sufficient to capture an adequate amount of light radiation from the plasma for performing spectral analysis.

Adjustable delay generator 170 effectively serves as a master timing source to provide independent signals for gating the photo-multiplier tube (PMT) and the detector on/off together for a predetermined duration in a coincident manner that assures detection of light emissions from the plasma at the same time and for the same duration. During the time that detector 150 is activated, delay generator 170 provides an on/off gating pulse to PMT 140 of substantially the same duration. This arrangement permits obtaining a selectable time-resolved analysis of the light radiation emitted from an evolving plasma plume. The timing of the triggering signals provided by delay generator 170 to detector controller 160 and PMT 140 are individually set such that detector 150 and PMT 140 are both activated to receive light from the same plasma event and over the same period during the evolution of the plasma.

A narrow-band interference filter 135 is used in front of PMT 140 to allow only passage of light wavelengths that are characteristic of one or more closely spaced atomic emissions of predetermined elements of the material comprising the part or object being examined, without passing emission wavelengths that are characteristic of the vaporized deposit or other foreign materials. If the amount of light passing through the filter exceeds a predetermined threshold, implying that at least some substrate material of the object beneath the deposit was vaporized, the PMT triggers shutter control electronics 136 which operate a shutter 122 to block the light output from laser 110 so that no further ablation of the surface can occur.

More explicitly, on/off gating of PMT 140 is controlled by adjustable delay generator 170 so as to be synchronized with the on/off gating of detector 150. Narrow-band interference filter 135 allows passage of only the predominant atomic emission wavelength(s) characteristic of the elemental composition of the examined part or object (126), but does not allow passage of emission wavelengths characteristic of a deposit or foreign substance on its surface. If (or whenever) material of the examined object 126 (i.e., the substrate/material of the object which lies beneath a surface deposit) becomes vaporized by a laser pulse, only atomic emissions from the resulting plasma indicative of the object material will be passed through to the PMT to generate a signal that triggers shutter control 136 for closing the mechanical shutter device 122.

Shutter control 136 may comprise conventional control circuitry commonly used for operating a mechanical shutter. Once any one LPS laser pulse has begun to vaporize and ablate the substrate material of the examined part or object, any further pulses of light from the laser are blocked due to activation of the shutter. In this context, one of ordinary skill in the art will appreciate that alternative means may also be used to prevent the laser from causing any further ablation to the object, such as, for example, cutting power to the laser in response to a signal from PMT 140. One of ordinary skill in the art will also appreciate that all of the electronic components and the optical components of system 100, including spectrometer 130, are preferred to be as lightweight and compact in construction as reasonably possible so as to enhance the portability of the system.

In one example embodiment of the invention as depicted in FIG. 1, a laptop/portable computing device 190 having an integral display, storage and modem is coupled to the output of detector controller 160 via a conventional IEEE-232 serial interface. The emission spectra from one or more plasma events are analyzed in real-time and displayed or saved by computer 190 for future evaluation. Various commercial software packages for performing such analyses are available and may be used for programming computer 190 for collecting, resolving, displaying and archiving emission spectra data obtained from spectrometer detector 150. For example, a Microsoft Windows® based software package such as Princeton Instruments' Winspec or Acton Research's SpectraSense™, available from Roper Scientific, Inc., may be used.

Once an emission spectral profile of the plasma is created, a comparison and matching of the spectral profile is performed in situ either manually or automatically against a reference source of known emission spectra to determine the elemental constituents of the deposit. A database containing reference spectral profiles of selected elements and/or compounds may be created and stored, for example, within portable computer 190 for in situ access and display. Alternatively, portable computer 190 may be provided with conventional means to access a remotely located database containing emission spectra information through a conventional wired or wireless communications link, a telephone line or via the Internet.

In one example embodiment, spectral information comprising intensity and wavelength data acquired using portable system 100 is calibrated and saved in a data file on computer 190. The data file is analyzed, for example, by using a conventional software peak-fitting routine, which may also reside on computer 190. The values of fitted peaks determined by the peak fitting routine are saved in another data file. A further software routine may be used to compare the values of peaks from this file to the values of peaks in reference spectral profiles that were previously prepared and stored in the computer onboard memory or, alternatively, in remote database accessible by the computer via, for example, a wired or wireless communications link. When a comparison match occurs that is within certain predetermined limits of error, the name of the matching element and/or a computed value indicative of the degree of error in the match is displayed on computer 190 and associated or stored with that data file for future use.

Figure 2:
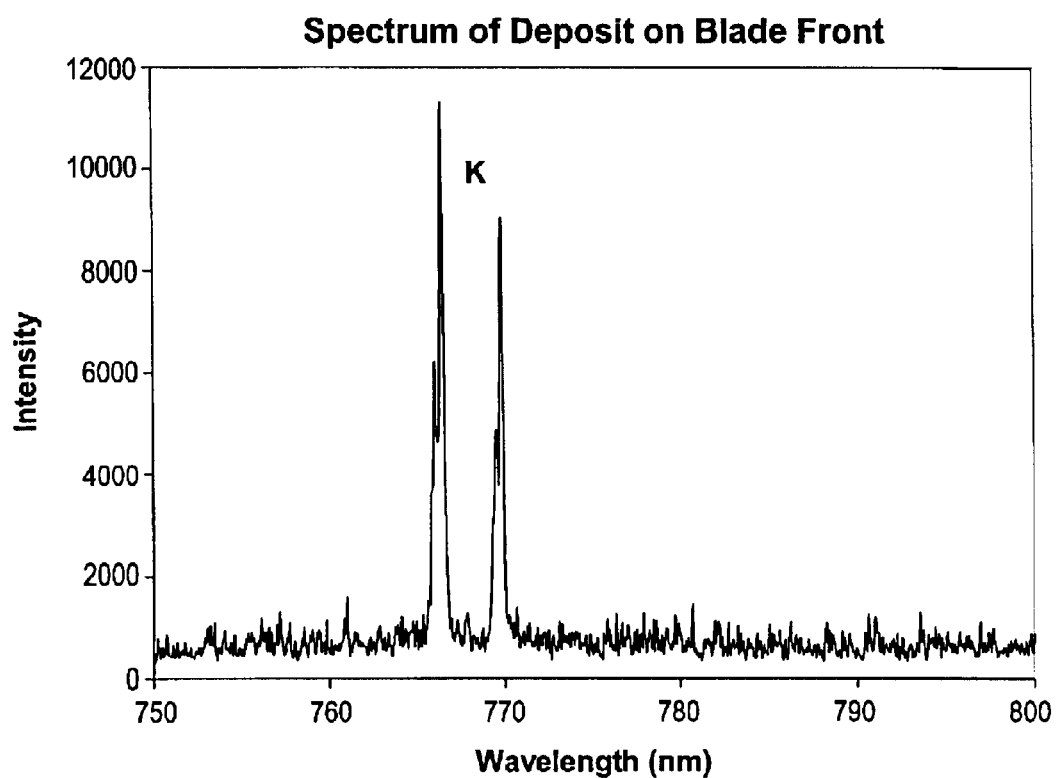
FIG. 2 is an example wavelength vs. intensity graph of a plasma spectrum obtained from a deposit on a turbine compressor blade.

FIG. 2 shows an example graph of a spectrum of plasma light radiation obtained from a deposit vaporized from the surface of a turbine compressor blade using diagnostic system 100. In this example, the spectrum produced from the plasma of the vaporized deposit indicates the presence of potassium (K), which is readily identifiable by the strong atomic emissions at the 766.49 nm and 769.90 nm wavelengths (i.e., atomic emissions at this particular pair of wavelengths is unique to potassium).

Figure 3:
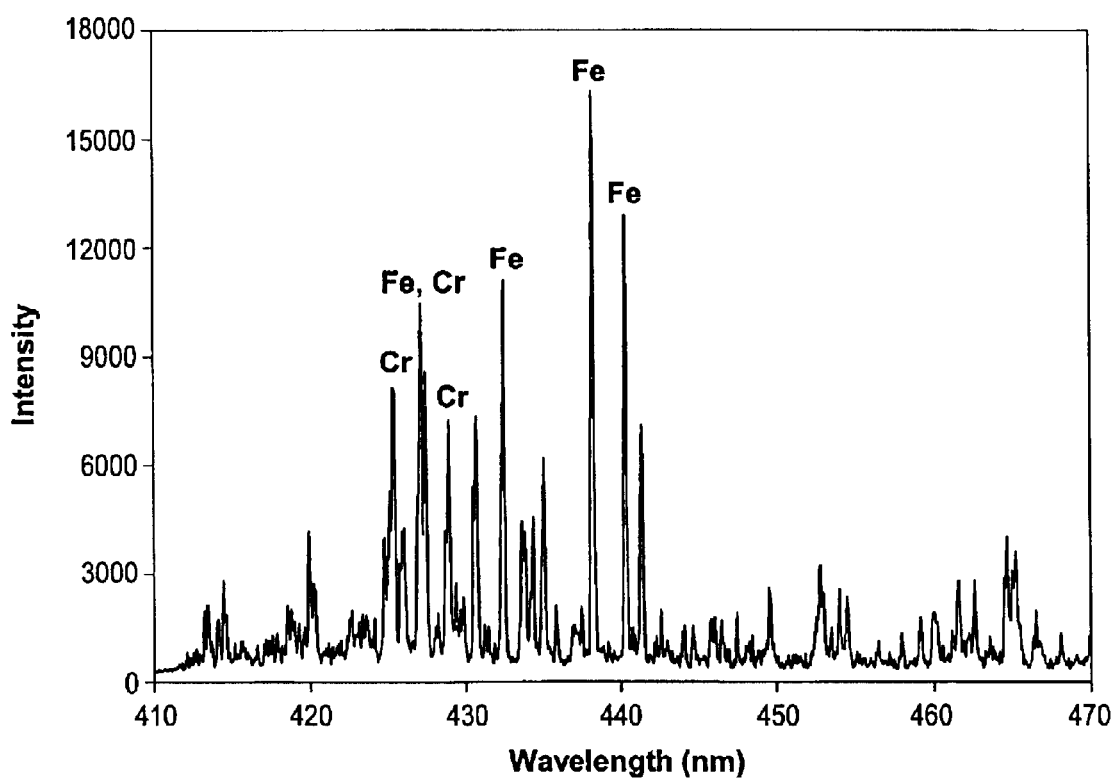
FIG. 3 is an example wavelength vs. intensity graph of a plasma spectrum obtained from the substrate material of a turbine compressor blade.

FIG. 3 shows an example of atomic emissions that are characteristic of the elemental materials comprising a typical turbine compressor blade. The two most prevalent elements in the compressor blade substrate material are iron (Fe) and chromium (Cr), as evidenced by the labeled intensity peaks. One or more of these characteristic emissions may be selected as representative of the compressor blade substrate material; e.g., two atomic emissions from Al at 425.43 nm and 428.97 nm Filter 135 of system 100 is judiciously selected or designed accordingly so as to pass only one or both of these representative emissions to PMT 140. If these representative emissions are detected above a predetermined threshold by PMT 140, it will trigger the closure of mechanical shutter 122 so as to preclude further laser pulses reaching and possibly damaging the turbine blade.

Figures 4A, 4B:
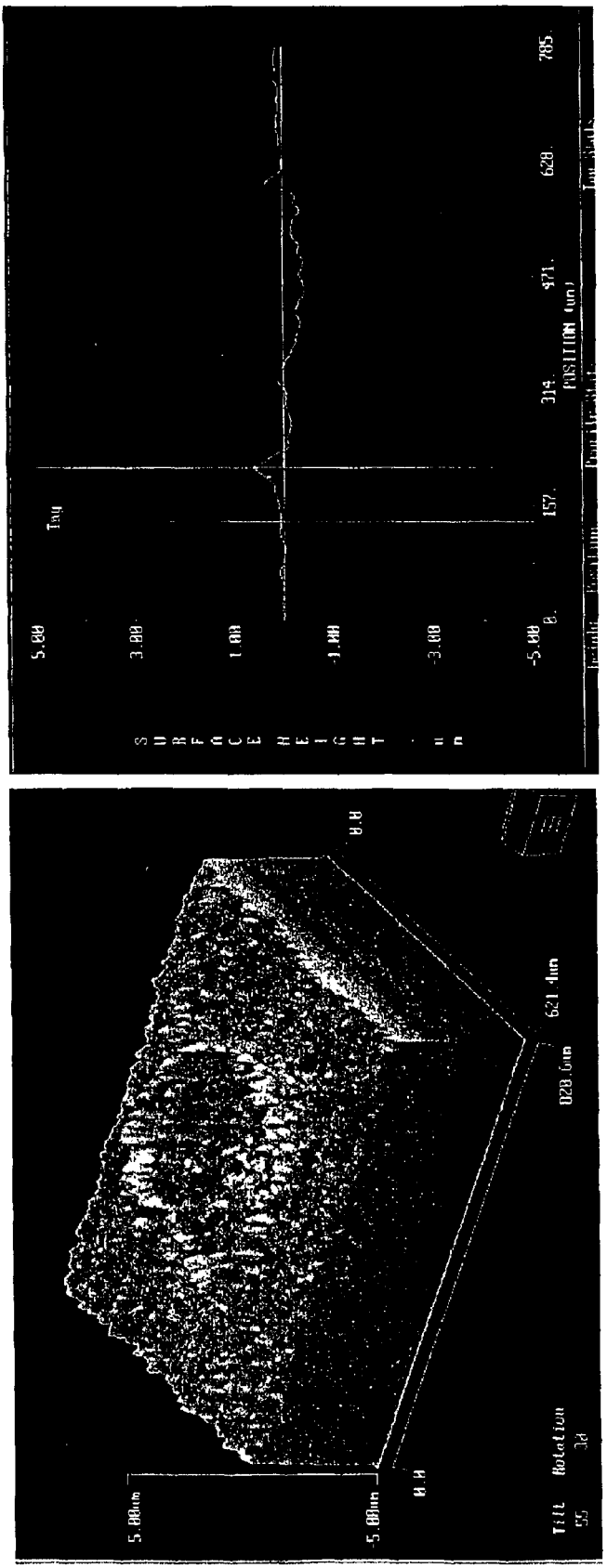
FIGS. 4A and 4B illustrate the effect of incident laser pulses on the surface of a compressor blade, as obtained via optical profilometric analysis.

FIGS. 4A and 4B show the results of an optical profilometric analysis performed upon a sample of turbine compressor blade substrate material after five 18.5 mJ laser pulses, each focused to a 400 micron spot, were delivered to the surface of the turbine blade. Typically, the amount of laser pulse energy needed in LPS applications using nanosecond pulse lasers is on the order of 1–20 mJ. In this example, a 18.5 mJ laser pulse was chosen as being in the general working range of a typical high peak power laser that might be used for performing LPS on industrial machinery and equipment such as turbine compressor blades or the like. FIG. 4A shows the three-dimensional profile of a sample of the substrate after the five laser pulses have struck the surface. FIG. 4B illustrates a graph of surface height vs. position along an example line bisecting the focal spot. As evident from the depicted profilometric analysis, less than 500 nm of material was ablated from the substrate material surface after delivery of five laser pulses (i.e., an effective ablation rate of less than 100 nm/pulse). Accordingly, if ablation to the underlying surface substrate material is detected after exposure to a single laser pulse of 18.5 mJ or less (or in a worst case of up to five of such laser pulses), then ablative damage to the substrate material beneath a deposit on an object may be significantly limited and, in most cases, any existing ablation can be considered as negligible.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for performing Laser Plasma Spectroscopy (LPS) on a foreign substance or deposit found on a surface of a machine part or object, comprising the steps of:
    a) collecting light emitted from a plasma generated by focusing a predetermined amount of laser output light energy onto a surface of a machine part or object;
    b) directing at least a portion of light collected in step (a) to an optical filter that only passes one predetermined narrow wavelength band containing elemental atomic emission wavelengths that are characteristic of one or more elemental components of a characteristic material comprising said machine part or object;
    c) detecting an amount of light passed by said filter; and
    d) preventing further laser output light energy from impinging on the machine part or object when light in step (c) is detected;
    wherein an identification of one or more elemental constituents of the foreign substance or deposit found on a surface of a machine part or object is obtained through LPS without incurring further ablation to the characteristic material of the machine part or object that lies beneath the foreign substance or deposit.

2. The method of claim 1 wherein a plasma is generated from one or more pulses of laser output light energy.

3. The method of claim 2 wherein each pulse of laser output light energy is focused to an intensity of 1 GW/cm$^2$ or greater.

4. The method of claim 1 wherein preventing step (d) comprises activating a shutter to block said laser output energy.

5. The method of claim 4 wherein the shutter comprises a mechanical shutter.

6. The method of claim 1 wherein said portion of light in step (b) is directed to the optical filter by using one branch portion of a bifurcated fiber optic cable.

7. The method of claim 1 wherein said portion of light in step (b) is directed to the optical filter by a beam splitter.

8. The method of claim 1 wherein 10% of light collected in step (a) is directed to the optical filter.

9. The method of claim 1 further comprising the step of directing a portion of light collected in step (a) to a spectrometer device.

10. The method of claim 2 wherein further pulses of laser output light energy are prevented from impinging on the machine part or object after a single laser output light energy pulse produces light detected in step (c).

11. The method of claim 1 wherein the machine part or object is a turbine compressor blade.

12. The method of claim 1 wherein the machine part or object is a component in power generating equipment.

13. A portable LPS apparatus for providing in situ elemental analysis of a foreign substance or deposit located on a surface of a machine part or object, comprising:

a laser device;

a spectrometer device;

a semiconductor array detector device coupled to the spectrometer device for detecting a spectrum of light resolved by the spectrometer device;

a low-level light detecting device;

an optical fiber probe for delivering the laser device output light energy to a location on a surface of a machine part or object that is remote from the LPS apparatus; means for collecting light radiation emitted from a plasma created during LPS;

a timing source for controlling on/off gating of the array detector and the low-level light detecting device at a substantially identical time and duration during an LPS plasma evolution event;

means for providing a portion of collected plasma light radiation to the low-level light detecting device;

a bandpass filter arrangement for limiting the portion of collected plasma light radiation provided to the low-level light detecting device to one predetermined narrow wavelength band encompassing an elemental atomic emission wavelength or wavelengths that are characteristic of one or more elemental components of a characteristic material comprising the machine part or object; and a shutter device for preventing laser output light energy from reaching a surface of said machine part or object in response to light of a specific range of wavelengths detected by the low-level light detecting device;

wherein identification of the elemental constituents of the foreign substance or deposit is obtained without incurring substantial ablation of a machine part or object substrate material underlying the foreign substance or deposit.

14. The apparatus of claim 13 further comprising a laser light impenetrable housing which encloses one or more optical components.

15. The apparatus of claim 13 wherein the optical fiber probe is contained within a flexible protective sheath.

16. The apparatus as defined by claim 15 wherein the protective sheath incorporates a lens positioned at an output end of the fiber and a sheath that extends beyond the lens at least an amount equal to a focal length of the lens.

17. The apparatus of claim 13 further comprising a portable computing device for performing an analysis on data collected by the array detector to determine an emission spectra profile of collected plasma light radiation.

18. The system according to claim 17 wherein the analysis is performed by the portable computing device substantially in real time.

19. The system according to claim 17 wherein the emission spectra profile of collected plasma light radiation is displayed by the computing device as a graph of intensity vs. wavelength.

20. The apparatus of claim 13 wherein the machine part or object is a turbine compressor blade.

21. The apparatus of claim 13 wherein the machine part or object is a component in power generating equipment.

* * * * *

UNITED STATES PATENT AND TRADEMARK OFFICE
CERTIFICATE OF CORRECTION

PATENT NO. : 6,762,836 B2
DATED : July 13, 2004
INVENTOR(S) : Benicewicz et al.

It is certified that error appears in the above-identified patent and that said Letters Patent is hereby corrected as shown below:

Column 8,
Line 23, delete "collecting tight" and insert -- collecting light --

Signed and Sealed this

Fourteenth Day of December, 2004

JON W. DUDAS
*Director of the United States Patent and Trademark Office*